(12) United States Patent
Chen et al.

(10) Patent No.: US 10,415,085 B2
(45) Date of Patent: Sep. 17, 2019

(54) NUCLEOTIDE SEQUENCE, UNIVERSAL REVERSE PRIMER, UNIVERSAL RT PRIMER, METHOD FOR DESIGNING PRIMER AND MIRNA DETECTION METHOD

(71) Applicant: Quark Biosciences, Taiwan, Inc, Hsinchu County (TW)

(72) Inventors: Wei-Ming Chen, Hsinchu County (TW); Shih-Ting Kang, Hsinchu County (TW)

(73) Assignee: Quark Biosciences Taiwan, Inc., Hsinchu County (TW)

( * ) Notice: Subject to any disclaimer, the term of this patent is extended or adjusted under 35 U.S.C. 154(b) by 289 days.

(21) Appl. No.: 15/170,914

(22) Filed: Jun. 1, 2016

(65) Prior Publication Data

US 2017/0022544 A1 Jan. 26, 2017

Related U.S. Application Data (60) Provisional application No. 62/169,563, filed on Jun. 2, 2015.

(51) Int. Cl.
*G16B 20/00* (2019.01)
*C12Q 1/686* (2018.01)
*C12Q 1/6853* (2018.01)

(52) U.S. Cl.
CPC .......... *C12Q 1/686* (2013.01); *C12Q 1/6853* (2013.01); *C12Q 2600/158* (2013.01); *C12Q 2600/178* (2013.01)

(58) Field of Classification Search
CPC ...................................................... C12Q 1/68
See application file for complete search history.

(56) References Cited

FOREIGN PATENT DOCUMENTS

| CN | 102154505 | 8/2011 |
|---|---|---|
| CN | 102301011 | 12/2011 |
| CN | 104630222 | 5/2015 |

OTHER PUBLICATIONS

Busk et al., A tool for design of primers for microRNA-specific quantitative RT-qPCR, BMC Bioinformatics. Jan. 28, 2014 28;15:29. doi: 10.1186/1471-2105-15-29.*
Ingrid Balcells et al., "Specific and sensitive quantitative RT-PCR of miRNAs with DNA primers", BMC Biotechnology 2011 11:70, Jun. 25, 2011, pp. 1-11.
Peter K Busk, "A tool for design of primers for microRNA-specific quantitative RT-qPCR", BMC Bioinformatics 2014 15:29, Jan. 28, 2014, pp. 1-9.
Cirera Salicio et al., "Quantification of miRNAs by a simple and specific qPCR method", Methods in Molecular Biology 2014 1182, Jun. 2014, pp. 73-81.
"Office Action of Taiwan Counterpart Application", dated Dec. 30, 2016, p. 1-p. 9, in which the listed references were cited.

* cited by examiner

*Primary Examiner* — Aaron A Priest
(74) *Attorney, Agent, or Firm* — JCIPRNET (57) ABSTRACT

A nucleotide sequence having SEQ ID NO:1, a universal reverse primer having SEQ ID NO:2, a universal RT primer, a method for designing primer, and a miRNA detection method are provided. In the miRNA detection method, the universal RT primer is used for the cDNA synthesis of a miRNA sample and the universal reverse primer is used for cDNA molecule amplification in qPCR quantitative detection. The universal reverse primer sequence, the nucleotide sequence, and the design rules are used in the method for designing primer, so as to design a primer for qPCR quantitative detection.

5 Claims, 1 Drawing Sheet

Specification includes a Sequence Listing.

NUCLEOTIDE SEQUENCE, UNIVERSAL REVERSE PRIMER, UNIVERSAL RT PRIMER, METHOD FOR DESIGNING PRIMER AND MIRNA DETECTION METHOD

CROSS-REFERENCE TO RELATED APPLICATION

This application claims the priority benefits of U.S. provisional application Ser. No. 62/169,563, filed on Jun. 2, 2015. The entirety of the above-mentioned patent application is hereby incorporated by reference herein and made a part of this specification.

BACKGROUND OF THE INVENTION

Field of the Invention

The invention relates to a nucleotide sequence, a universal reverse primer, a universal RT primer, a method for designing primer, and a miRNA detection method, and more particularly, to a nucleotide sequence, a universal reverse primer, a universal RT primer, a method for designing primer, and a miRNA detection method for miRNA detection, quantification, and expression profiling.

Description of Related Art miRNAs are highly conserved non-coding RNAs having a length between 18 to 25 nucleotides, and regulate gene expression of an organism. In recent years, research results have shown that miRNA expression is implicated in many diseases, especially cancer, and miRNAs function as oncogenes or tumor suppressor genes which play important roles in pathophysiology of human cancer. More specifically, the level/expression of miRNA in cancer patients' bodily fluids can be used as a tool for cancer diagnosis and prognosis, which makes miRNAs novel, robust cancer biomarkers. Moreover, various cancer diagnostic tools have been developed based on the difference in miRNA expression between healthy individuals and cancer patients. Therefore, the materials and methods used for miRNA detection, quantification, and expression profiling are important and critical.

In prior art, methods of detecting and quantifying miRNA include Northern blot hybridization, cloning, microarray gene chip analysis, and next-generation sequencing technology. In comparison to prior art, the quantitative real-time reverse transcription PCR (qRT-PCT) method has higher sensitivity and specificity.

Currently, various different qRT-PCR methods have been developed, and these methods can mainly be divided into the following two types. The first type is performing cDNA synthesis using a stem-loop RT primer, and quantifying miRNA using a miRNA specific probe or a universal probe. The second method is to perform cDNA synthesis using a linear universal RT primer and quantify miRNA using a miRNA specific forward primer, a RT-primer specific reverse primer, and a double-stranded DNA intercalating dye.

Regarding the qRT-PCR method, since the reverse transcription primer of the first method contains a one stem-loop structure, better specificity is achieved, but the cost of the miRNA specific probe or the universal probe used is higher. The second method does not require a probe, and therefore costs can be further reduced. However, the specificity of the linear universal RT primer used in the second method is worse than that of the stem-loop reverse transcription primer of the first type, and the current commercial universal RT primer may need to be further modified.

Based on the above, how to increase the specificity and the sensitivity of the linear universal RT primer and the reverse primer and achieving the characteristics of reduced cost and ease of use so as to detect, quantify, and analyze the performance of miRNA is an important topic.

SUMMARY OF THE INVENTION

The invention provides a nucleotide sequence, a universal reverse primer, a universal RT primer, and a method for designing primer suitable for a qRT-PCR method of miRNA detection, quantification, and expression profiling, wherein the universal reverse primer, the universal RT primer, and the primer designed by the method for designing primer have better specificity and sensitivity, and the characteristics of reduced cost and ease of use are achieved at the same time, and additional oligonucleotide modification is not required for the primers.

The invention provides a nucleotide sequence having SEQ ID NO:1 for designing a forward primer in miRNA qPCR detection and performing cDNA molecule amplification with a reverse primer.

The invention provides a universal reverse primer having SEQ ID NO:2 to perform cDNA molecule amplification with a forward primer in miRNA qPCR detection.

In an embodiment of the invention, the Tm value of the universal reverse primer is 59.1° C.

The invention provides a universal RT primer for performing cDNA synthesis on a miRNA sample to be tested, wherein the universal RT primer is a nucleotide sequence represented by the following general formula:

$$R\text{-}(dT)nVN$$

wherein R is a nucleotide sequence at the 5' end and is SEQ ID NO:2, (dT)n is an n number of continuous thymine residues of the intermediate portion, n is 19, VN is the sequence formed by the nucleotide residue at the 3' end, V is adenine residue, guanine residue, or cytosine residue, and N is adenine residue, guanine residue, cytosine residue, or thymine residue.

The invention provides a method for designing primer, wherein the primer is used for miRNA qPCR detection, and the method for designing primer includes the following steps. The sequence similarity between a miRNA to be tested and other miRNA in the same species is confirmed. When the sequence similarity between the miRNA to be tested and the other miRNA in the same species is less than 90%, the forward primer is designed by a first design method, and the first design method includes a first adjustment step and a first confirmation step. In the first adjustment step, the Tm difference between the forward primer and the universal reverse primer having SEQ ID NO:2 is made to not exceed 2° C., and when the Tm value of the forward primer is less than 57, nucleotide sequences having SEQ ID NO:1 are sequentially added at the 5' end, such that the Tm value of the forward primer reaches 57° C. to 61° C. In the first confirmation step, ΔG of the dimer of the forward primer is confirmed to be greater than −7.5 kcal/mol. When ΔG of the dimer is less than −7.5 kcal/mol, the forward primer sequence of the dimer region is deleted to avoid the region in which the dimer is formed, and the first adjustment step and the first confirmation step are repeated. When the sequence similarity between the miRNA to be tested and the other miRNA in the same species is higher than 90%, the forward primer and the reverse primer are designed by a second design method, and the second design method includes an overlap design step, a second adjustment step, and a second confirmation step. In the overlap design step, the locations of nucleotide difference between the miRNA to be tested and the other miRNA in the same species are compared, and the last nucleotide residue at the 3' end of the forward primer and the reverse primer is designed to the location of nucleotide difference. If the miRNA to be tested and the other miRNA in the same species still cannot be distinguished, then an overlapping base is added forward to the forward primer or the reverse primer, or an overlapping base is added to both the forward primer and the reverse primer. In the second adjustment step, the Tm difference between the forward primer and the reverse primer is made to not exceed 2° C., and when the Tm value of the forward primer is less than 55, nucleotide sequences having SEQ ID NO:1 are sequentially added at the 5' end, and when the Tm value of the reverse primer is less than 55, nucleotide sequences having SEQ ID NO:2 are sequentially added at the 5' end, such that the Tm values of the forward primer and the reverse primer reach 55° C. to 61° C. In the second confirmation step, ΔG of the dimers of the forward primer and the reverse primer is confirmed to be greater than −7.5 kcal/mol. When ΔG of the dimers is less than −7.5 kcal/mol, the nucleotide sequences having SEQ ID NO:1 added to the 5' end of the forward primer are replaced, wherein the nucleotide sequences having SEQ ID NO:1 have different nucleotide residue combinations, so as to avoid the region in which the dimer is formed, and the second adjustment step and the second confirmation step are repeated. When the second design method cannot avoid the region in which the dimer is formed, if the dimer issue is caused by the reverse primer, then a third design method is performed, and if the dimer issue is caused by the forward primer, then a fourth design method is performed. The third design method includes extending the length of the 3' end of the forward primer and reducing the length of the 3' end of the reverse primer, so as to avoid the region in which the dimer is formed, wherein the location of nucleotide difference is designed within the last four nucleotides at the 3' end of the forward primer or the reverse primer, and if the Tm value is insufficient after the length of the 3' end of the reverse primer is reduced, then nucleotide sequences having SEQ ID NO:2 are sequentially added at the 5' end of the reverse primer. The fourth design method includes extending the length of the 3' end of the reverse primer and reducing the length of the 3' end of the forward primer, so as to avoid the region in which the dimer is formed, wherein the location of nucleotide difference is designed within the last four nucleotides at the 3' end of the forward primer or the reverse primer, and if the Tm value is insufficient after the length of the 3' end of the forward primer is reduced, then nucleotide sequences having SEQ ID NO:1 are sequentially added at the 5' end of the forward primer.

In an embodiment of the invention, cDNA molecule amplification is performed on the forward primer and the universal reverse primer having SEQ ID NO:2 designed by the first design method in qPCR detection.

In an embodiment of the invention, in the first design method, the dimer of the forward primer includes a self-dimer of the forward primer or a hetero-dimer formed between the forward primer and the universal reverse primer having SEQ ID NO:2.

In an embodiment of the invention, in the second design method, the dimers of the forward primer and the reverse primer include a self-dimer of each of the forward primer and the reverse primer or a hetero-dimer formed between the forward primer and the reverse primer.

In an embodiment of the invention, in the first design method, when the region in which the dimer is formed cannot be avoided, the forward primer and the reverse primer are designed by the following method to avoid the region in which the dimer is formed, wherein the reverse primer is not the universal reverse primer having SEQ ID NO:2. The method of extending the forward primer includes extending the length of the 3' end of the forward primer and reducing the length of the 3' end of the reverse primer to avoid the region in which the dimer is formed, wherein the length of the forward primer is 12 to 18 bases. Alternatively, the method of extending the reverse primer includes extending the length of the 3' end of the reverse primer and reducing the length of the 3' end of the forward primer to avoid the region in which the dimer is formed, wherein the length of the reverse primer is 12 to 18 bases.

The invention provides a miRNA detection method including the following steps. First, a poly-A tail is added to a miRNA to be tested in a sample. Next, cDNA synthesis is performed on the miRNA to be tested using a universal RT primer. Next, cDNA molecule amplification is performed on the forward primer and the reverse primer designed by the method for designing primer of the invention. In particular, the universal RT primer is a nucleotide sequence represented by the following general formula: R−(dT)nVN, wherein R is a nucleotide sequence at the 5' end and is SEQ ID NO:2, (dT)n is an n number of continuous thymine residues of the middle portion, n is 19, VN is the sequence forming by the nucleotide residue at the 3' end, V is adenine residue, guanine residue, or cytosine residue, and N is adenine residue, guanine residue, cytosine residue, or thymine residue.

In an embodiment of the invention, the reverse primer is a universal reverse primer having SEQ ID NO:2.

Based on the above, the invention provides a nucleotide sequence, a universal reverse primer, a universal RT primer, a method for designing primer, and a miRNA detection method, and in the miRNA detection method, the universal RT primer is used to perform cDNA synthesis on a miRNA sample, the universal reverse primer is used to amplify a cDNA molecule in qPCR quantitative detection, and the method for designing primer adopts the universal reverse primer, the nucleotide sequence, and the design rules to design the primer used in qPCR quantitative detection. The universal RT primer, the universal reverse primer, and the primer designed by the method for designing primer of the invention have better specificity and sensitivity, and have the characteristics of reduced cost and ease of use at the same time, and additional modification is not needed for the primers.

In order to make the aforementioned features and advantages of the invention more comprehensible, embodiments are described in detail below.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF THE EMBODIMENTS

The invention provides a nucleotide sequence, a universal reverse primer, a universal RT primer, and a method for designing primer suitable for a qRT-PCR method of miRNA detection, quantification, and expression profiling. In the following, the terms used in the specification are defined first.

"ΔG" is Gibbs free energy, and is a thermodynamic function describing chemical reactions. The stability of the dimer structure can be represented by ΔG, which is the energy required to break the dimer. A greater ΔG negative value (defined as ΔG<−7.5 kcal/mol in the invention) indicates the presence of a stable and undesirable dimer structure, which adversely affects the PCR reaction.

"qPCR" or "real-time quantitative PCR" (real-time quantitative polymerase chain reaction) refers to an experimental method of using PCR to amplify and quantify target DNA at the same time. Quantification is performed using a plurality of measuring chemical substances (including, for instance, fluorescent dye of SYBR® green or fluorescent reporter oligonucleotide probe of Taqman probe), and real-time quantification is performed with the amplified DNA accumulated in the reaction after every amplification cycle.

"qRT-PCR" (real-time quantitative reverse transcription polymerase chain reaction) refers to using cDNA generated in a reverse transcription reaction of a sample to be tested as a quantitative reverse transcription polymerase chain reaction of a starting DNA template in a PCR amplification process, and then performing qPCR to quantify a miRNA to be tested.

"Tm" (melting temperature) is generally defined as the temperature when 50% of a double helix formed between a nucleotide and a complementary nucleotide chain is dissociated into a single strand. Regarding the length of the nucleotide and the composition of the nucleotide, the content of G and C nucleotides in the nucleotide sequence is an important factor affecting Tm. The measurement method of Tm is a known technique in the art of the invention is therefore not repeated herein.

"cDNA" (complementary DNA) refers to complementary DNA generated by performing reverse transcription on an RNA template using reverse transcriptase.

"Nucleotide" includes adenine (A), guanine (G), cytosine (C), and thymine (T).

"miRNA" is the synonymous abbreviation of microRNA.

"Ct value" is the number of amplification cycles when fluorescence intensity starts to be significantly increased in a qPCR operation process.

The invention provides a method for designing primer, and a primer designed by the method is suitable for a qPCR method for miRNA detection. In the method for designing primer of the invention, the sequence similarity between a miRNA to be tested and other miRNA in the same species is first confirmed, the sequences of the miRNA to be tested and the other miRNA in the same species are compared, the ratio of nucleotide sequence base number difference is evaluated, and whether the first design method or the second design method is performed is determined according to the sequence similarity. More specifically, relevant information of the other miRNA in the same species can be obtained from relevant technical literature in the art or a public database such as miRBase database. When the sequence similarity is less than 90%, the forward primer is designed by the first design method; when the sequence similarity is higher than 90%, the forward primer and the reverse primer are designed by the second design method.

The sequence design of the forward primer generally contains 12 to 18 nucleotide residues that are the same as those at the 5' end of the miRNA sequence to be tested. The sequence design of the reverse primer generally contains 2 to 8 nucleotide residues complementary to the 3' end of the miRNA sequence to be tested, and contains 19 thymine residues and tails having different lengths (SEQ ID NO:2 sequence), wherein the 19 thymine residues and tails are the same as a portion of the universal RT primer. Next, one method is selected from the first design method to the fourth design method according to the design rules of the method for designing primer provided in the invention to design the primer.

<First Design Method>

The first design method includes a first adjustment step and a first confirmation step.

First, the first adjustment step is performed to make the Tm value difference between a forward primer and a universal reverse primer having the sequence 5'-CAACTCAGGTCGTAGGCAATTCGT-3' (SEQ ID NO:2) not exceed 2° C., wherein the Tm value of the universal reverse primer is 59.1° C. More specifically, when the Tm value of the forward primer is less than 57° C., nucleotide sequences having the sequence CGWTSSRCRC (SEQ ID NO:1) are sequentially added at the 5' end to make the Tm value of the forward primer lie between 57° C. and 61° C. When the Tm value of the sequence of the forward primer itself is between 57° C. and 61° C., nucleotide sequences do not need to be sequentially added at the 5' end.

It should be mentioned that, in the nucleotide sequences having the sequence CGWTSSRCRC (SEQ ID NO:1), W is adenine residue or thymine residue (A or T), S is guanine residue or cytosine residue (G or C), and R is adenine residue or guanine residue (A or G). By sequentially adding nucleotide sequences having SEQ ID NO:1 at the 5' end of the forward primer, the Tm value of the forward primer can more readily reach the desired range and high specificity can be achieved, such that the forming of a self-dimer and a hetero-dimer can be further prevented.

Next, the first confirmation step is performed to confirm whether a self-dimer is formed for the forward primer or whether a hetero-dimer is formed between the forward primer and the universal reverse primer.

If ΔG of the self-dimer and the hetero-dimer is greater than −7.5 kcal/mol, then the design of the forward primer is completed. When ΔG of at least one of the self-dimer and the hetero-dimer is less than −7.5 kcal/mol, the forward primer sequence of the dimer region is deleted to avoid the region in which the dimers are forming, and the first adjustment step and the first confirmation step are repeated.

If the first design method cannot avoid the region in which the dimers are formed, then the forward primer and the reverse primer are designed by the following method to avoid the region in which the dimers are formed, wherein the reverse primer is not the universal reverse primer having SEQ ID NO:2. The method of extending the forward primer includes extending the length of the 3' end of the forward primer and reducing the length of the 3' end of the reverse primer to avoid the region in which the dimers are formed, wherein the sequence length of the forward primer is about 12 to 18 bases. Alternatively, the method of extending the reverse primer includes extending the length of the 3' end of the reverse primer and reducing the length of the 3' end of the forward primer to avoid the region in which the dimers are formed, wherein the length of the reverse primer is about 12 to 18 bases.

After the forward primer is designed using the first design method, in the miRNA detection method, cDNA synthesis is performed on a miRNA to be tested using a universal RT primer, and then cDNA molecule amplification is performed using the forward primer and the universal reverse primer having SEQ ID NO:2 designed by the first design method in qPCR quantitative detection.

More specifically, the universal RT primer is a nucleotide sequence represented by the following general formula:

$$R\text{-}(dT)nVN$$

wherein R is a nucleotide sequence at the 5' end and is SEQ ID NO:2, (dT)n is an n number of continuous thymine residues of the middle portion, n is 19, VN is a sequence formed by the nucleotide residue at the 3' end, V is adenine residue, guanine residue, or cytosine residue, and N is adenine residue, guanine residue, cytosine residue, or thymine residue.

<Second Design Method>

The second design method includes an overlap design step, a second adjustment step, and a second confirmation step.

First, the overlap design step is performed to compare the locations of nucleotide difference between a miRNA to be tested and other miRNA in the same species, and the last nucleotide residue at the 3' end of the forward primer and the reverse primer is designed to the nucleotide residues of the locations of nucleotide difference. More specifically, if the miRNA to be tested and the other the miRNA in the same species still cannot be distinguished by overlapping one nucleotide residue, then an overlapping base can be added forward to the forward primer or the reverse primer, or an overlapping base is added to both the forward primer and the reverse primer.

Next, the second adjustment step is performed to make the Tm difference between the forward primer and the reverse primer not exceed 2° C. More specifically, when the Tm value of the forward primer is less than 55° C., nucleotide sequences having SEQ ID NO:1 are sequentially added at the 5' end of the forward primer, and when the Tm value of the reverse primer is less than 55° C., nucleotide sequences having SEQ ID NO:2 are sequentially added at the 5' end, such that the Tm values of the forward primer and the reverse primer reach between 55° C. and 61° C. When the Tm values of the sequences of the forward primer and the reverse primer themselves are between 55° C. and 61° C., nucleotide sequences do not need to be sequentially added at the 5' end.

Next, the second confirmation step is performed to confirm whether a self-dimer is formed for the forward primer and the reverse primer or whether a hetero-dimer is formed between the forward primer and the reverse primer.

If ΔG of the self-dimer and the hetero-dimer is greater than −7.5 kcal/mol, then the designs of the forward primer and the reverse primer are completed. If ΔG of at least one of the self-dimer and the hetero-dimer is less than −7.5 kcal/mol, then nucleotide sequences having SEQ ID NO:1 (having different nucleotide residue combinations) added to the 5' end of the forward primer are replaced, and the second adjustment step and the second confirmation step are repeated.

After the forward primer and the reverse primer are designed using the second design method, in the miRNA detection method, cDNA synthesis is performed on the miRNA to be tested using a universal RT primer, and then cDNA molecule amplification is performed using the forward primer and the reverse primer designed by the second design method in qPCR quantitative detection. The universal RT primer used is the same as the universal RT primer above and is therefore not repeated herein.

When the second design method cannot avoid the region in which the dimers are formed, the third design method or the fourth design method is performed. If the dimer issue is caused by the reverse primer, then the third design method is performed, and if the primer issue is caused by the forward primer, then the fourth design method is performed.

<Third Design Method>

The third design method includes extending the length of the 3' end of the forward primer and reducing the length of the 3' end of the reverse primer, so as to avoid the region in which the dimers are forming, wherein the locations of nucleotide difference of the miRNA to be tested and the other miRNA in the same species need to be designed within the last four nucleotides at the 3' end of the forward primer or the reverse primer. After the length of the 3' end of the reverse primer is reduced, if the Tm value is insufficient, then nucleotide sequences having SEQ ID NO:2 are sequentially added at the 5' end. As a result, the probability of successfully distinguishing highly similar miRNA sequences can be increased. Moreover, in the third design method, if the dimer issue cannot be avoided, then the universal reverse primer having SEQ ID NO:2 can also be used to replace the reverse primer.

<Fourth Design Method>

The fourth design method includes extending the length of the 3' end of the reverse primer and reducing the length of the 3' end of the forward primer, so as to avoid the region in which the dimers are formed, wherein the locations of nucleotide difference of the miRNA to be tested and the other miRNA in the same species need to be designed within the last four nucleotides at the 3' end of the forward primer or the reverse primer. After the length of the 3' end of the forward primer is reduced, if the Tm value is insufficient, then nucleotide sequences having SEQ ID NO:1 are sequentially added at the 5' end. As a result, the probability of successfully distinguishing highly similar miRNA sequences can be increased.

Figure 1:
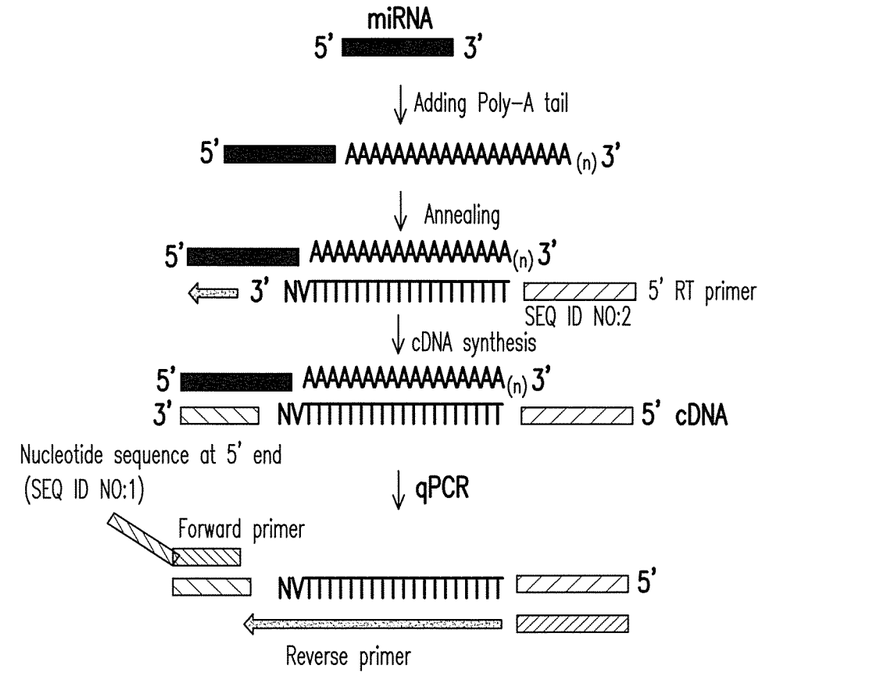
FIG. 1 is a flow schematic of a miRNA detection method of the invention.

The invention also provides a miRNA detection method. FIG. 1 is a flow schematic of a miRNA detection method of the invention, which is described in detail with reference to FIG. 1 below.

Referring to FIG. 1, in the miRNA detection method of the invention, a poly-A tail is first added to a miRNA to be tested in a sample using poly(A) polymerase, wherein the poly(A) polymerase adds an adenine residue to the 3' end of the miRNA to be tested. Next, via the hybridization with a universal RT primer, the universal RT primer and the miRNA to be tested carrying a poly-A tail are annealed. The universal RT primer used is the same as the universal RT primer above and is therefore not repeated herein. Next, cDNA synthesis is performed on the miRNA to be tested using the universal RT primer. Lastly, a qPCR reaction is performed. The cDNA molecule is amplified using the forward primer and the reverse primer designed by the method for designing primer of the invention to perform real-time miRNA quantitative detection.

More specifically, if the primer is designed using the first design method, then the forward primer and the reverse primer used to perform cDNA molecule amplification are respectively the forward primer and the universal reverse primer having SEQ ID NO:2 designed by the first design method. If the primer is designed using the second design method, then the forward primer and the reverse primer used to perform cDNA molecule amplification are respectively the forward primer and the reverse primer designed by the second design method.

In the following, each of the design methods is described in detail via experimental examples. However, the following experimental examples are not intended to limit the invention.

Experimental Examples

To prove that the method for designing primer provided in the invention can improve the specificity of the primer, the following experimental examples are provided.

First Design Method

A miRNA detection method was performed by using synthetic oligonucleotides hsa-miR-589-5p as a template and using a forward primer hsa-miR-589-5p-F and a universal reverse primer having SEQ ID NO:2 designed by the first design method as a specific primer pair.

The experimental steps of the cDNA synthesis are as follows. First, x μl (2 ng) miRNA, 0.5 μl 200 μM universal RT primer, 1 μl 1 mM ATP (New England Biolads Inc.), 1 μl 10 mM dNTP (New England Biolads Inc.), 2 μl 10×M-MuLV reverse transcriptase reaction buffer, 1 μl (200 U/μl) M-MuLV reverse transcriptase (New England Biolads Inc.), and 1 μl (5 U/μl) E. coli Poly(A) polymerase (New England Biolads Inc.) were mixed, and then water was added to 20 μl to form a cDNA mixture. Next, the cDNA mixture was incubated at 37 t for 1 hour, and then M-MuLV reverse transcriptase was deactivated at 80 t for 5 minutes. The resulting cDNA product could be stored at −20° C. before use.

qPCR was performed using PanelStation™ (made by Quark Biosciences, Inc.), wherein the reaction conditions are as follows. 2 μl of above RT reaction product and 30 μl 2×GoTaq® qPCR Master Mix (Promega) were mixed, and then water was added to 60 μl to form a mixture. The mixture was reacted at 95° C. for 3 minutes, and then 39 cycles were performed at 95° C. for 36 seconds and 60° C. for 72 seconds.

It can be known from the experimental results that, the forward primer hsa-miR-589-5p-F and the universal reverse primer having SEQ ID NO:2 can successfully amplify a specific product with a Ct value of 26.5.

```
hsa-miR-589-5p:
                                        (SEQ ID NO: 3)
5'-TGAGAACCACGTCTGCTCTGAG-3' hsa-miR-589-5p-F:
                                        (SEQ ID NO: 4)
GCTGAGAACCACGTCTGCTC
``` wherein the underline marker of the forward primer hsa-miR-589-5p-F is the nucleotide sequences having SEQ ID NO:1 sequentially added in the first adjustment step.

Measured data of forward primer property: Tm=58.2, self-dimer ΔG=−6.3 kcal/mol; hetero-dimer ΔG=−6.73 kcal/mol.

Second Design Method

A miRNA detection method was performed by using synthetic oligonucleotides hsa-miR-18a-5p and hsa-miR-18b-5p having very high sequence similarity as a template, and a forward primer hsa-miR-18a-5p-F and a reverse primer hsa-miR-18a-5p-R designed by the second design method were used as a specific primer pair, wherein the cDNA synthesis and the qPCR experimental method are as described in the experimental example of the first design method and are therefore not repeated herein.

```
hsa-miR-18a-5p:
                                        (SEQ ID NO: 5)
5'-TAAGGTGCATCTAGTGCAGATAG-3' hsa-miR-18b-5p:
                                        (SEQ ID NO: 6)
5'-TAAGGTGCATCTAGTGCAGTTAG-3'
``` wherein the underline markers of the synthetic oligonucleotides hsa-miR-18a-5p and hsa-miR-18b-5p are the locations of nucleotide difference.

```
hsa-miR-18a-5p-F:
                                        (SEQ ID NO: 7)
5'-GCTAAGGTGCATCTAGTGCAGA-3' hsa-miR-18a-5p-R:
                                        (SEQ ID NO: 8)
5'-TCGTAGGCAATTCGTTTTTTTTTTTTTTTTTTTCTAT-3'
``` wherein the underline marker of the forward primer hsa-miR-18a-5p-F is the nucleotide sequences having SEQ ID NO:1 sequentially added in the second adjustment step, and the underline marker of the reverse primer hsa-miR-18a-5p-R is the nucleotide sequences having SEQ ID NO:2 sequentially added in the second adjustment step.

Measured data of forward primer and reverse primer property: forward primer Tm=56.7° C.; reverse primer Tm=55.9° C.; self-dimers of forward primer and reverse primer ΔG>−7.5 kcal/mol; hetero-dimer ΔG>−7.5 kcal/mol.

It can be known from the experimental results of Table 1 that, the forward primer hsa-miR-18a-5p-F and the reverse primer hsa-miR-18a-5p-R can successfully distinguish the synthetic oligonucleotides hsa-miR-18a-5p and hsa-miR-18b-5p.

TABLE 1

| Template | Ct average value |
|---|---|
| Synthetic oligonucleotides hsa-miR-18a-5p | 24.8 |
| Synthetic oligonucleotides hsa-miR-18b-5p | 30.8 |

A qPCR reaction was respectively performed on the synthetic oligonucleotides hsa-miR-18a-5p and the synthetic oligonucleotides hsa-miR-18b-5p using the forward primer hsa-miR-18a-5p-F and the reverse primer hsa-miR-18a-5p-R designed by the second design method, and each qPCR reaction had 2,500 technical repeats. By calculating the specificity of the forward primer hsa-miR-18a-5p-F and the reverse primer hsa-miR-18a-5p-R with a logistic regression model using the fluorescence intensity and the Ct value of the qPCR results, an accuracy of 95.5% can be obtained, indicating the synthetic oligonucleotides hsa-miR-18a-5p and the synthetic oligonucleotides hsa-miR-18b-5p can be successfully distinguished.

Third Design Method

A miRNA detection method was performed by using synthetic oligonucleotides hsa-miR-19a-3p and hsa-miR-19b-3p having very high sequence similarity as a template, and the forward primer hsa-miR-19a-3p-V1F and the reverse primer hsa-miR-19a-3p-V1R designed by the second design method and a forward primer hsa-miR-19a-3p-V2F and a universal reverse primer having SEQ ID NO:2 designed by the third design method were respectively used as specific primer pairs, wherein the cDNA synthesis and the qPCR experimental method are as described in the experimental example of the first design method and are therefore not repeated herein.

```
hsa-miR-19a-3p:
                                        (SEQ ID NO: 9)
5'-TGTGCAAATCTATGCAAAACTGA-3' hsa-miR-19b-3p:
                                       (SEQ ID NO: 10)
5'-TGTGCAAATCCATGCAAAACTGA-3'
``` wherein the underline markers of the synthetic oligonucleotides hsa-miR-19a-3p and hsa-miR-19b-3p are the locations of nucleotide difference.

```
hsa-miR-19a-3p-V1F:
                                       (SEQ ID NO: 11)
5'-GTTGCACGCTGTGCAAATCT-3' hsa-miR-19a-3p-V1R:
                                       (SEQ ID NO: 12)
5'-GCAATTCGTTTTTTTTTTTTTTTTTTTCAGTTTTGCATA-3'
``` wherein the underline marker of the forward primer hsa-miR-19a-3p-F is the nucleotide sequences having SEQ ID NO:1 sequentially added in the second adjustment step, and the underline marker of the reverse primer hsa-miR-19a-3p-R is the nucleotide sequences having SEQ ID NO:2 sequentially added in the second adjustment step.

Measured data of forward primer and reverse primer property: forward primer Tm=56.9; reverse primer Tm=58; self-dimer of forward primer ΔG=−10.33 kcal/mol; self-dimer of reverse primer ΔG-7.5 kcal/mol; hetero-dimer ΔG=−10.94 kcal/mol.

```
hsa-miR-19a-3p-V2F:
                                       (SEQ ID NO: 13)
5'-CGTTCGACGCTGTGCAAATCTAT-3'
``` wherein the right-side underline marker of the forward primer hsa-miR-19a-3p-V2F is the increase in the length of the forward primer at the 3' end, the difference is kept within the last 4 nucleotide sequences at the 3' end, and the left-side underline marker is the nucleotide sequences having SEQ ID NO:1 sequentially added in the second adjustment step.

In the third design method, since the dimer issue cannot be avoided, the universal reverse primer having SEQ ID NO:2 is used to replace the reverse primer.

Measured data of forward primer and universal reverse primer property: forward primer Tm=57.8; universal reverse primer Tm=59.1; self-dimer of forward primer ΔG=−7.05 kcal/mol; self-dimer of universal reverse primer ΔG=−5.36 kcal/mol; hetero-dimer ΔG=−6.53 kcal/mol.

It can be known from the experimental results of Table 2 that, since the forward primer hsa-miR-19a-3p-V1F and the reverse primer hsa-miR-19a-3p-V1R designed by the second design method show significant dimer issue (ΔG of the dimer is less than −7.5 kcal/mol), a qPCR reaction could not be performed. In comparison, the forward primer hsa-miR-19a-3p-V2F and the universal reverse primer having SEQ ID NO:2 designed by the third design method can successfully distinguish the synthetic oligonucleotides hsa-miR-19a-3p and hsa-miR-19b-3p.

TABLE 2

| Template | Primer pair | |
|---|---|---|
| | hsa-miR-19a-3p-V1F/ hsa-miR-19a-3p-V1R Ct average value | hsa-miR-19a-3p-V2F/ universal reverse primer having SEQ ID NO: 2 Ct average value |
| Synthetic oligonucleotides hsa-miR-19a-3p | | 24.7 |
| Synthetic oligonucleotides hsa-miR-19b-3p | | 31.7 |

A qPCR reaction was respectively performed on the synthetic oligonucleotides hsa-miR-19a-3p and the synthetic oligonucleotides hsa-miR-19b-3p using the forward primer hsa-miR-19a-3p-V2F and the universal reverse primer having SEQ ID NO:2 designed by the third design method, and each qPCR reaction had 2,500 technical repeats. By calculating the specificity of the forward primer hsa-miR-19a-3p-V2F and the universal reverse primer having SEQ ID NO:2 with a logistic regression model using the fluorescence intensity and the Ct value of the qPCR results, an accuracy of 99.1% can be obtained, indicating the synthetic oligonucleotides hsa-miR-19a-3p and the synthetic oligonucleotides hsa-miR-19b-3p can be successfully distinguished.

Based on the above, the invention provides a nucleotide sequence, a universal reverse primer, a universal RT primer, and a method for designing primer, wherein the nucleotide sequence having SEQ ID NO:1 can more readily make the Tm value of the forward primer reach the desired range, and has high specificity, and multiple combinations of nucleotide sequences having SEQ ID NO:1 can further prevent the forming of a dimer. The universal RT primer thereof has stability and specificity, and is suitable for all miRNA analyses, and performing a cDNA synthesis reaction by using the single universal RT primer has the advantages of reducing experimental samples, time, and technical variation. Moreover, the method for designing primer of the invention is suitable for different primer design methods for miRNA family (sequence similarity>90%) and non-family (sequence similarity<90%), and prevents the forming of a dimer, such that the designed primer has better specificity and sensitivity, and a specific product can be successfully amplified, and miRNA sequences having very high sequence similarity can be successfully distinguished. Moreover, the characteristics of reduced cost and ease of use are achieved, and additional modification is not needed for the primers.

Although the invention has been described with reference to the above embodiments, it will be apparent to one of ordinary skill in the art that modifications to the described embodiments may be made without departing from the essence of the invention. Accordingly, the scope of the invention is defined by the attached claims not by the above detailed descriptions.

What is claimed is:

1. A method for designing primer, wherein the primer is used for miRNA qPCR detection, the method for designing primer comprising:

confirming a sequence similarity between a miRNA to be tested and other miRNA in the same organismic species, designing a forward primer using a first design method when the sequence similarity is less than 90%, and a sequence design of the forward primer contains 12 to 18 nucleotide residues that are the same as those at a 5' end of the miRNA to be tested, the first design method comprising:

a first adjustment step to make a Tm difference between the forward primer and a universal reverse primer having SEQ ID NO:2 not exceed 2° C., and when the Tm value of the forward primer is less than 57° C., nucleotide sequences having SEQ ID NO:1 are sequentially added at a 5' end, such that the Tm value of the forward primer reaches between 57° C. and 61° C.; and a first confirmation step to confirm ΔG of a dimer of the forward primer is greater than −7.5 kcal/mol, wherein when ΔG of the dimer is less than −7.5 kcal/mol, a forward primer sequence of a dimer region is deleted to avoid a region in which the dimer is formed, and the first adjustment step and the first confirmation step are repeated, designing a forward primer and a reverse primer using a second design method when the sequence similarity is greater than 90%, the second design method comprising:

providing the forward primer and the reverse primer, wherein the forward primer contains nucleotide residues that are the same as those a 5' end of the miRNA sequence to be tested, and the reverse primer contains nucleotide residues complementary to the 3' end of the miRNA sequence to be tested and 19 thymine residues;

an overlap design step to compare and find nucleotide differences between the sequence of the miRNA to be tested and the other miRNA in the same organismic species, and the last nucleotide residue at a 3' end of the forward primer and the reverse primer is designed to a site of the nucleotide differences, if the miRNA to be tested and the other miRNA in the same species still cannot be distinguished, then a next base to the site of the nucleotide differences is added forward to the forward primer or the reverse primer, or a next base to the site of the nucleotide differences is added to both the forward primer and the reverse primer;

a second adjustment step to make the Tm difference between the forward primer and the reverse primer not exceed 2° C., and when the Tm value of the forward primer is less than 55° C., nucleotide sequences having SEQ ID NO:1 are sequentially added at the 5' end, and when the Tm value of the reverse primer is less than 55° C., nucleotide sequences having SEQ ID NO:2 are sequentially added at the 5' end, such that the Tm values of the forward primer and the reverse primer reach between 55° C. and 61° C.; and a second confirmation step to confirm ΔG of the dimers of the forward primer and the reverse primer is greater than −7.5 kcal/mol, wherein when ΔG of the dimers is less than −7.5 kcal/mol, nucleotide sequences having SEQ ID NO:1 added to the 5' end of the forward primer are replaced to avoid the region in which the dimers are formed, and the second adjustment step and the second confirmation step are repeated, when the second design method cannot avoid the region in which the dimers are formed, if a dimer issue is caused by the reverse primer, then a third design method is performed, and if the primer issue is caused by the forward primer, then a fourth design method is performed, the third design method comprising:

extending a length of the 3' end of the forward primer and reducing a length of the 3' end of the reverse primer to avoid the region in which the dimers are formed, wherein the locations of nucleotide difference are designed within the last four nucleotides at the 3' end of the forward primer or the reverse primer, and if the Tm value is less than 55° C. after the length of the 3' end of the reverse primer is reduced, then nucleotide sequences having SEQ ID NO:2 are sequentially added at the 5' end of the reverse primer, the fourth design method comprising:

extending the length of the 3' end of the reverse primer and reducing the length of the 3' end of the forward primer to avoid the region in which the dimers are formed, wherein the locations of nucleotide difference are within the last four nucleotides at the 3' end of the forward primer or the reverse primer, and if the Tm value is insufficient after the length of the 3' end of the forward primer is reduced, then nucleotide sequences having SEQ ID NO:1 are sequentially added at the 5' end of the forward primer, and performing a synthesis step to synthesize the primer designed by the method for designing primer.

2. The method for designing primer of claim 1, wherein in the first design method, the dimer of the forward primer comprises a self-dimer of the forward primer or a heterodimer formed between the forward primer and the universal reverse primer having SEQ ID NO:2.

3. The method for designing primer of claim 1, wherein in the second design method, the dimers of the forward primer and the reverse primer comprise a self-dimer of each of the forward primer and the reverse primer or a heterodimer formed between the forward primer and the reverse primer.

4. The method for designing primer of claim 1, wherein in the first design method, when the region in which the dimers are formed cannot be avoided, the forward primer and the reverse primer are designed by the following method to avoid the region in which the dimers are formed, wherein the reverse primer is not the universal reverse primer having SEQ ID NO:2;
- a method of extending the forward primer comprises extending the length of the 3' end of the forward primer and reducing the length of the 3' end of the reverse primer to avoid the region in which the dimers are formed, wherein the length of the forward primer is 12 to 18 bases, or
- a method of extending the reverse primer comprises extending the length of the 3' end of the reverse primer and reducing the length of the 3' end of the forward primer to avoid the region in which the dimers are formed, wherein the length of the reverse primer is 12 to 18 bases.

5. The method for designing primer of claim 1, comprising:
   adding a poly-A tail to a miRNA to be tested in a sample;
   performing cDNA synthesis on the poly-A-tailed miRNA to be tested using a universal RT primer; and
   performing cDNA molecule amplification using the synthesized forward primer and the synthesized reverse primer,
   wherein the universal RT primer is a nucleotide sequence represented by the following general formula:

$R-(dT)nVN$ wherein R is a nucleotide sequence at the 5' end and is SEQ ID NO:2, (dT)n is an n number of continuous thymine residues of an intermediate portion, n is 19, VN is a sequence formed by a nucleotide residue at the 3' end, V is adenine residue, guanine residue, or cytosine residue, and N is adenine residue, guanine residue, cytosine residue, or thymine residue.

* * * * *

SEQUENCE LISTING

<160> NUMBER OF SEQ ID NOS: 13

<210> SEQ ID NO 1
<211> LENGTH: 10

```
<212> TYPE: DNA
<213> ORGANISM: Artificial Sequence
<220> FEATURE:
<223> OTHER INFORMATION: Synthetic
<220> FEATURE:
<221> NAME/KEY: Misc_feature
<222> LOCATION: (3)..(3)
<223> OTHER INFORMATION: w is a or t
<220> FEATURE:
<221> NAME/KEY: Misc_feature
<222> LOCATION: (5)..(5)
<223> OTHER INFORMATION: s is g or c
<220> FEATURE:
<221> NAME/KEY: Misc_feature
<222> LOCATION: (6)..(6)
<223> OTHER INFORMATION: s is g or c
<220> FEATURE:
<221> NAME/KEY: Misc_feature
<222> LOCATION: (7)..(7)
<223> OTHER INFORMATION: r is a or g
<220> FEATURE:
<221> NAME/KEY: Misc_feature
<222> LOCATION: (9)..(9)
<223> OTHER INFORMATION: r is a or g

<400> SEQUENCE: 1 cgwtssrcrc                                                          10

<210> SEQ ID NO 2
<211> LENGTH: 24
<212> TYPE: DNA
<213> ORGANISM: Artificial Sequence
<220> FEATURE:
<223> OTHER INFORMATION: Synthetic

<400> SEQUENCE: 2
caactcaggt cgtaggcaat tcgt                                          24

<210> SEQ ID NO 3
<211> LENGTH: 22
<212> TYPE: DNA
<213> ORGANISM: Artificial Sequence
<220> FEATURE:
<223> OTHER INFORMATION: Synthetic

<400> SEQUENCE: 3
tgagaaccac gtctgctctg ag                                            22

<210> SEQ ID NO 4
<211> LENGTH: 20
<212> TYPE: DNA
<213> ORGANISM: Artificial Sequence
<220> FEATURE:
<223> OTHER INFORMATION: Synthetic

<400> SEQUENCE: 4
gctgagaacc acgtctgctc                                               20

<210> SEQ ID NO 5
<211> LENGTH: 23
<212> TYPE: DNA
<213> ORGANISM: Artificial Sequence
<220> FEATURE:
<223> OTHER INFORMATION: Synthetic

<400> SEQUENCE: 5
taaggtgcat ctagtgcaga tag                                           23

<210> SEQ ID NO 6
```

```
<211> LENGTH: 23
<212> TYPE: DNA
<213> ORGANISM: Artificial Sequence
<220> FEATURE:
<223> OTHER INFORMATION: Synthetic

<400> SEQUENCE: 6
taaggtgcat ctagtgcagt tag                                              23

<210> SEQ ID NO 7
<211> LENGTH: 22
<212> TYPE: DNA
<213> ORGANISM: Artificial Sequence
<220> FEATURE:
<223> OTHER INFORMATION: Synthetic

<400> SEQUENCE: 7
gctaaggtgc atctagtgca ga                                               22

<210> SEQ ID NO 8
<211> LENGTH: 38
<212> TYPE: DNA
<213> ORGANISM: Artificial Sequence
<220> FEATURE:
<223> OTHER INFORMATION: Synthetic

<400> SEQUENCE: 8
tcgtaggcaa ttcgtttttt tttttttttt ttttctat                              38

<210> SEQ ID NO 9
<211> LENGTH: 23
<212> TYPE: DNA
<213> ORGANISM: Artificial Sequence
<220> FEATURE:
<223> OTHER INFORMATION: Synthetic

<400> SEQUENCE: 9
tgtgcaaatc tatgcaaaac tga                                              23

<210> SEQ ID NO 10
<211> LENGTH: 23
<212> TYPE: DNA
<213> ORGANISM: Artificial Sequence
<220> FEATURE:
<223> OTHER INFORMATION: Synthetic

<400> SEQUENCE: 10
tgtgcaaatc catgcaaaac tga                                              23

<210> SEQ ID NO 11
<211> LENGTH: 20
<212> TYPE: DNA
<213> ORGANISM: Artificial Sequence
<220> FEATURE:
<223> OTHER INFORMATION: Synthetic

<400> SEQUENCE: 11
gttgcacgct gtgcaaatct                                                  20

<210> SEQ ID NO 12
<211> LENGTH: 41
<212> TYPE: DNA
<213> ORGANISM: Artificial Sequence
<220> FEATURE:
<223> OTHER INFORMATION: Synthetic

<400> SEQUENCE: 12
```

```
gcaattcgtt tttttttttt tttttttttc agttttgcat a                              41

<210> SEQ ID NO 13
<211> LENGTH: 23
<212> TYPE: DNA
<213> ORGANISM: Artificial Sequence
<220> FEATURE:
<223> OTHER INFORMATION: Synthetic

<400> SEQUENCE: 13
cgttcgacgc tgtgcaaatc tat                                                  23
```